US010836690B1

(12) United States Patent
Duff et al.

(10) Patent No.: US 10,836,690 B1
(45) Date of Patent: Nov. 17, 2020

(54) DEHYDROGENATION PROCESS AND SYSTEM WITH REACTOR RE-SEQUENCING

(71) Applicant: TPC Group LLC, Houston, TX (US)

(72) Inventors: Joseph G. Duff, League City, TX (US); David S. Hager, Houston, TX (US); Gilbert D. Valdez, Pearland, TX (US); Joseph A. Comeaux, Pearland, TX (US); Michael O. Nutt, Pearland, TX (US)

(73) Assignee: TPC Group LLC, Houston, TX (US)

( * ) Notice: Subject to any disclaimer, the term of this patent is extended or adjusted under 35 U.S.C. 154(b) by 0 days.

(21) Appl. No.: 16/587,161

(22) Filed: Sep. 30, 2019

Related U.S. Application Data (60) Provisional application No. 62/878,864, filed on Jul. 26, 2019.

(51) Int. Cl.
*C07C 4/06* (2006.01)
*C07C 5/333* (2006.01)
(Continued)

(52) U.S. Cl.
CPC ............. *C07C 5/3332* (2013.01); *B01J 8/025* (2013.01); *B01J 8/0285* (2013.01); *B01J 23/825* (2013.01); *C07C 4/06* (2013.01); *B01J 2208/025* (2013.01)

(58) Field of Classification Search
CPC ........ B01J 37/0201; B01J 37/03; B01J 37/04; B01J 37/18; B01J 38/12; C07C 11/06;
(Continued)

(56) References Cited

U.S. PATENT DOCUMENTS 4,172,854 A 10/1979 Ellis et al.
4,581,339 A 4/1986 Bhatt et al.
(Continued)

FOREIGN PATENT DOCUMENTS

GB 794089 A 4/1958
GB 823626 A 11/1959
WO 2018203233 A1 11/2018

OTHER PUBLICATIONS

Sanfilippo, et al., Hydrogenation and Dehydrogenation, Ullman's Encyclopedia of Industrial Chemistry, 2012, pp. 451-471, vol. 18, Wiley-VCH Verlag GmbH & Co. KgaA, Weinheim, Germany.
(Continued)

*Primary Examiner* — Sharon Pregler
(74) *Attorney, Agent, or Firm* — Michael Ferrell (57) ABSTRACT

A dehydrogenation system includes a plurality of dehydrogenation reactors valved to operate in alternating dehydrogenation modes and regeneration modes in a timed sequence in a system cycle by way of the plurality of valves; a digital programmable controller connected to the plurality of valves for sequencing the reactors; and means for determining the productivity characteristics of each reactor over a system cycle. The digital controller is operable to re-sequence the reactors to reduce either peak productivity or productivity deltas over an initial system cycle. After resequencing, production may be increased with the more uniform productivity profile of the re-sequenced system without exceeding system limits, such as compressor operating limits.

19 Claims, 7 Drawing Sheets

(51) Int. Cl.
*B01J 23/825* (2006.01)
*B01J 8/02* (2006.01)

(58) Field of Classification Search
CPC ....... C07C 11/09; C07C 5/322; C07C 5/3337; C07C 11/02; C07C 11/167; C07C 5/325
See application file for complete search history.

(56) References Cited

U.S. PATENT DOCUMENTS

| | | |
|---|---|---|
| 5,219,816 A | 6/1993 | Zou et al. |
| 7,271,307 B2 * | 9/2007 | Urbancic .............. C07C 5/3332 585/654 |
| 7,622,623 B2 | 11/2009 | Fridman et al. |
| 7,973,207 B2 | 7/2011 | Fridman et al. |
| 8,188,328 B2 | 5/2012 | Fridman et al. |
| 9,725,380 B2 * | 8/2017 | Fridman ............... C07C 5/3332 |
| 2013/0109897 A1 | 1/2013 | Morrison et al. |
| 2014/0163292 A1 | 6/2014 | Grüne et al. |
| 2014/0296606 A1 | 10/2014 | Weyne et al. |
| 2017/0252738 A1 | 9/2017 | Duff |
| 2019/0126242 A1 | 5/2019 | Xing et al. |
| 2019/0225563 A1 | 7/2019 | Pretz |

OTHER PUBLICATIONS

International Search Report and Written Opinion dated Aug. 11, 2020.

* cited by examiner

FIG. 5  INITIAL SEQUENCE 1,3,5,7,2,4,6

DEHYDROGENATION PROCESS AND SYSTEM WITH REACTOR RE-SEQUENCING

CLAIM FOR PRIORITY

This application is based on U.S. Provisional Application No. 62/878,864 of the same title, filed 26 Jul. 2019, the priority of which is hereby claimed and the disclosure of which is incorporated herein by reference.

TECHNICAL FIELD

The present invention relates generally to cyclic dehydrogenation processes and systems with multiple dehydrogenation reactors operating in alternating and synchronized production/regeneration modes. These processes include the dehydrogenation of alkanes over fixed beds of catalyst such as supported chromium, gallium, or platinum/tin or the like. The invention involves sequencing or re-sequencing the reactors to reduce fluctuation in production rates over a system cycle which allows productivity to be increased.

BACKGROUND

Hydrocarbon dehydrogenation processes are conventionally practiced with systems having compressors and absorbers serving a plurality of sequenced reactors which operate in alternating production/regeneration modes over a system repeating cycle. There is shown, for example, in GB 794,089, a process for catalytic dehydrogenation of hydrocarbons carried out wherein the catalyst is alternately contacted with a hydrocarbon charge and subjected to regeneration by combustion of carbonaceous deposits resulting from dehydrogenation of the hydrocarbon charge. Each of the operations are carried out in a battery of reactors operated in a timed sequence of substantially equal periods of hydrocarbon conversion and catalyst regeneration. The sequence of operations for each reactor is as follows: (1) hydrocarbon dehydrogenation, (2) steam purging to free catalyst and reaction vessel of hydrocarbon products, (3) catalyst regeneration in oxygen-containing gas, (4) evacuation and (5) reduction of oxidized catalyst in hydrogen-containing gas. An exemplary form of the dehydrogenation system is illustrated in FIG. 2 of GB 794,089. As there is shown, the system comprises five reactors, R, which are operated in a cycle such that two are simultaneously on stream for catalytic dehydrogenation, two are being subjected to regeneration of catalyst therein, and one is in a stage involving an operation such as evacuation, steam purge, hydrogen reduction or valve changes. The diagram in FIG. 3 of GB 794,089 shows how the reactors are operated on an approximately 22.5 minute cycle.

Another multi-reactor dehydrogenation system is shown in GB 823,626. According to the GB 823,626 specification, two or more 3-reactor batteries are used. An exemplary dehydrogenation system is illustrated in FIG. 2 of GB 823,626. As there is shown, the system comprises six reactors, R, which are arranged in two batteries of three reactors each and are operated in a sequence such that two, i.e., one reactor of each battery, are simultaneously on stream for catalytic dehydrogenation, two are being subjected to regeneration of catalyst therein, and two are in a stage involving an operation such as evacuation, steam purge, hydrogen reduction or valve changes. The diagram in FIG. 3 of GB 823,626 shows how the reactors are operated on a 15 minute repeating cycle. It will be noted from an inspection of the cycle chart of FIG. 3 of GB 823,626 that reactors 1 and 4, 2 and 5 and 3 and 6 are always in the same phase of a cycle. The desirability of such arrangements according to the GB 823,626 specification is dictated by the fact that the paired reactors are opposite each other, as shown in FIG. 2 of GB 823,626. Thus the gaseous materials charged to the paired reactors, and the gaseous materials withdrawn therefrom, will have equal distances of travel to the mains conducting the gases to and from the unit. The GB 823,626 specification further notes that staggered cycle times may be desirable in terms of reducing demands on associated auxiliaries such as pumps, compressors and the like since only one reactor at a time is making a transition.

Other dehydrogenation systems with programmable controllers are seen in U.S. Pat. Nos. 4,581,339 and 7,271,307, as well as WO 2018/203233.

It is appreciated from the prior art that multiple alternating reactors in a dehydrogenation system are on a fixed sequence of operation, that is, the reactors are always operated in the same successive order. This is based, in part, on the assumption that reactor performance in terms of conversion is equivalent in reactors of the same construction having the same catalyst, feed and operating conditions. It has been found, however, that like reactors may not perform in a substantially identical manner, especially as the catalyst ages. Significant differences can arise in pressure/volume requirements and productivity, which are not unrelated in a gaseous dehydrogenation system because the product stream has an additional mole of hydrogen for each mole of dehydrogenation product produced. Differences in pressure drop/volume requirements may overtax the downstream product compressor or upstream regeneration air compressor when multiple reactors exhibiting high productivity are operated concurrently in a production mode. This leads to system shut down when horsepower limitations are reached; and therefore limits productivity based on peak production over a cycle.

Likewise, productivity differences between reactors in a multi-reactor system can also lead to inefficiency, productivity and yield losses when the downstream product recovery equipment capacity, notably absorber capacity, is exceeded or underutilized. When product recovery capacity is exceeded, dehydrogenation product is flared and lost. When absorbers are underutilized, hydrogen is sorbed unnecessarily, increasing energy requirements of the system.

SUMMARY OF INVENTION

It has been found that by re-sequencing reactors in an alternating cyclical multi-reactor dehydrogenation system that substantial and unexpected increases in productivity are achieved. In fact, production rates are maximized by reducing peak conversion of the system in a repeating cycle. Aggregate productivity of the reactors is balanced to run closer to compressor capacities for an entire cycle and process swings are reduced, improving absorber performance. In a preferred embodiment, the invention involves resequencing the reactors to reduce peak conversion and reduce productivity deltas over a system cycle. A preferred system for implementing the present invention is a multi-fixed bed, adiabatic endothermic reaction system known in the art as a Houdry dehydrogenation system as is shown in GB 794,089 and GB 823,626.

Figure 1:
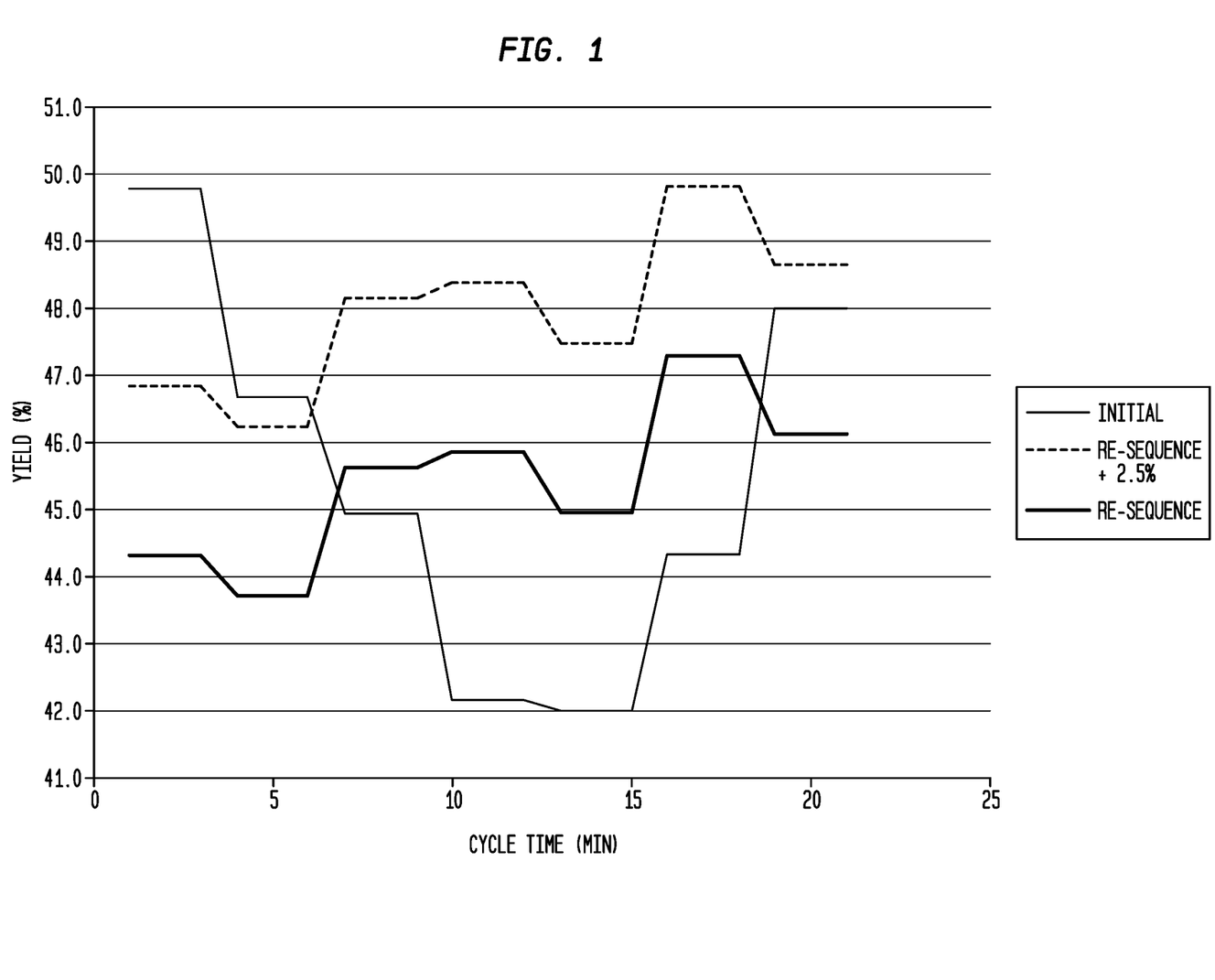
FIG. 1 is a plot of yield of isobutylene from isobutane over time in a multi-reactor system having a cycle time of about twenty-two (22) minutes.

The invention is better appreciated by reference to FIG. 1 which is a plot of isobutylene yield over time for different reactor sequences over a system repeating cycle in a seven reactor system operating on a twenty-two (22) minute system cycle. It is seen in an initial sequence, prior to re-sequencing, the system exhibits a yield delta of about 8% or so, but that after re-sequencing, the yield delta is reduced to half of that or less; while peak productivity is lowered by about 5% on a relative basis, corresponding to 2.5% yield reduction. Inasmuch as the system is limited by peak productivity prior to re-sequencing, productivity may be increased in the re-sequenced system by increasing feed rates of hydrocarbon, by raising temperature of the hydrocarbon charge, by raising the regeneration air temperature or decreasing inlet pressure to produce 5% more product on an hourly basis with the same equipment as is shown in the dashed productivity line in FIG. 1.

The invention may be realized in various ways by determining productivity of the various reactors and making adjustments to increase productivity. For instance, in a relatively simple system limited by a downstream product compressor to a yield value of 50, having 4 reactors, 2 reactors exhibiting yields of 50 operating simultaneously in dehydrogenation and regeneration modes alternating with two reactors having yield values of 40 operating simultaneously in dehydrogenation and regeneration modes over a cycle, the peak yield value will be 50 and the yield delta will be 10 over a system repeating operating cycle. If the reactors are re-sequenced over an operating cycle, with 1 reactor having a yield value of 50 and 1 reactor having a yield value of 40 being operating simultaneously in the same modes, the peak yield value is 45 and the yield delta goes away. Since the system can handle a yield value of 50, productivity can be increased by increasing feed rates of hydrocarbon, by raising temperature of the hydrocarbon charge, by raising the regeneration air temperature and so forth. Additional capacity is provided with no capital expense and only incremental operating expense.

In many embodiments the number of reactors on-line at any given time is more or less the same prior to and after re-sequencing; However, it is also possible to sequester an over-active reactor (hot spot) or an underperforming reactor in order to bring the system into better balance, if so desired.

Further details and advantages will become apparent from the discussion which follows.

BRIEF DESCRIPTION OF DRAWINGS

The invention is described in detail below with reference to the drawings wherein.

DETAILED DESCRIPTION

The invention is described in detail below in connection with the Figures for purposes of illustration, only. The invention is defined in the appended claims. Terminology used throughout the specification and claims herein is given its ordinary meaning as supplemented by the discussion immediately below, for example, "conversion", "selectivity" and yield are related by the mathematical definition X(conversion)*S(selectivity)=Y(yield), all calculated on a weight or molar basis; e.g. in a certain reaction, 90% of substance A is converted (consumed), but only 80% of it is converted to the desired substance B and 20% to undesired by-products, so conversion of A is 90%, selectivity for B 80% and yield of substance B is 72% (=90%*80%).

Characteristic peak productivity refers to the aggregate maximum productivity of the reactors at a given point in time during a production cycle at a given feed rate, temperatures of operation and so forth. The characteristic peak productivity of the re-sequenced reactors may be calculated instead of measured, if so desired.

Characteristic productivity delta is the difference between the aggregate maximum productivity of the reactors and the aggregate minimum productivity of the reactors during a system dehydrogenation cycle at a given feed rate, temperatures of operation and so forth. The minimum and maximum productivities of the re-sequenced reactors may be calculated instead of measured, if so desired.

Liquid hourly space velocity ("LHSV") based solely on the dehydrogenation reactant feed and is calculated as the hourly volumetric flow rate of liquid dehydrogenation reactant to the system divided by the volume of dehydrogenation catalyst beds in the multistage system, that is, in units of $hr^{-1}$. For purposes of Calculation of LHSV, the liquid density at atmospheric pressure and the boiling point of the reactant is used.

Unless otherwise indicated, "percent", "%" or like terminology refers to weight percent of a component or relative value to an initial value.

Productivity of the system at any given time refers to the aggregate rate of dehydrogenation product produced by the reactor system by the reactors operating in dehydrogenation mode, in kg per hour or in like units. For a given hydrocarbon feed rate, productivity is conveniently represented graphically by yield as is seen in FIG. 1, or may be approximated by conversion under a given set of conditions.

Generally speaking, terminology to the effect that the re-sequenced characteristic peak productivity is from 2% to 20% lower as compared to the initial characteristic peak productivity of the system refers to the productivity difference as compared to the characteristic initial peak productivity level. Thus, if peak yield decreases from 50% to 47.5% under a given set of conditions, we refer to the peak productivity as decreasing by 2.5/50 or 5% and so forth.

Terminology to the effect that the characteristic productivity delta of the re-sequenced system is at least 25% lower than as compared with the characteristic productivity delta of the initial system sequence refers to the change in the difference between the aggregate peak and minimum productivity over a system cycle. Thus, the initial system cycle has a peak yield of 50% and a minimum yield of 40% over a cycle and the re-sequenced system has a peak yield of 47.5% and a minimum of 42.5%, we refer to the characteristic productivity delta as decreasing from 10 to 5 or by 50% as compared to the initial system sequence.

When sequencing the reactors to achieve a productivity delta less than a certain value, the aggregate maximum and aggregate minimum production over a cycle is considered. Thus, a cycle having a peak productivity of 100 units and a minimum productivity of 80 units is said to have a productivity delta of 20 units or 20% of the peak productivity.

It will be appreciated from the foregoing and the discussion which follows that changes in characteristic peak productivity and characteristic productivity deltas can be conveniently expressed in percentages based on yield or conversion data from the reactors of the system. Thus, referring to FIG. 1 and Table 1, the re-sequenced system has a characteristic productivity delta of 3.6/7.8 or 46% lower as compared to the initial sequence. Moreover, the characteristic productivity delta of the re-sequenced system is 3.6/47.3 or 7.6% of the characteristic peak productivity of the re-sequenced system.

Figure 5:
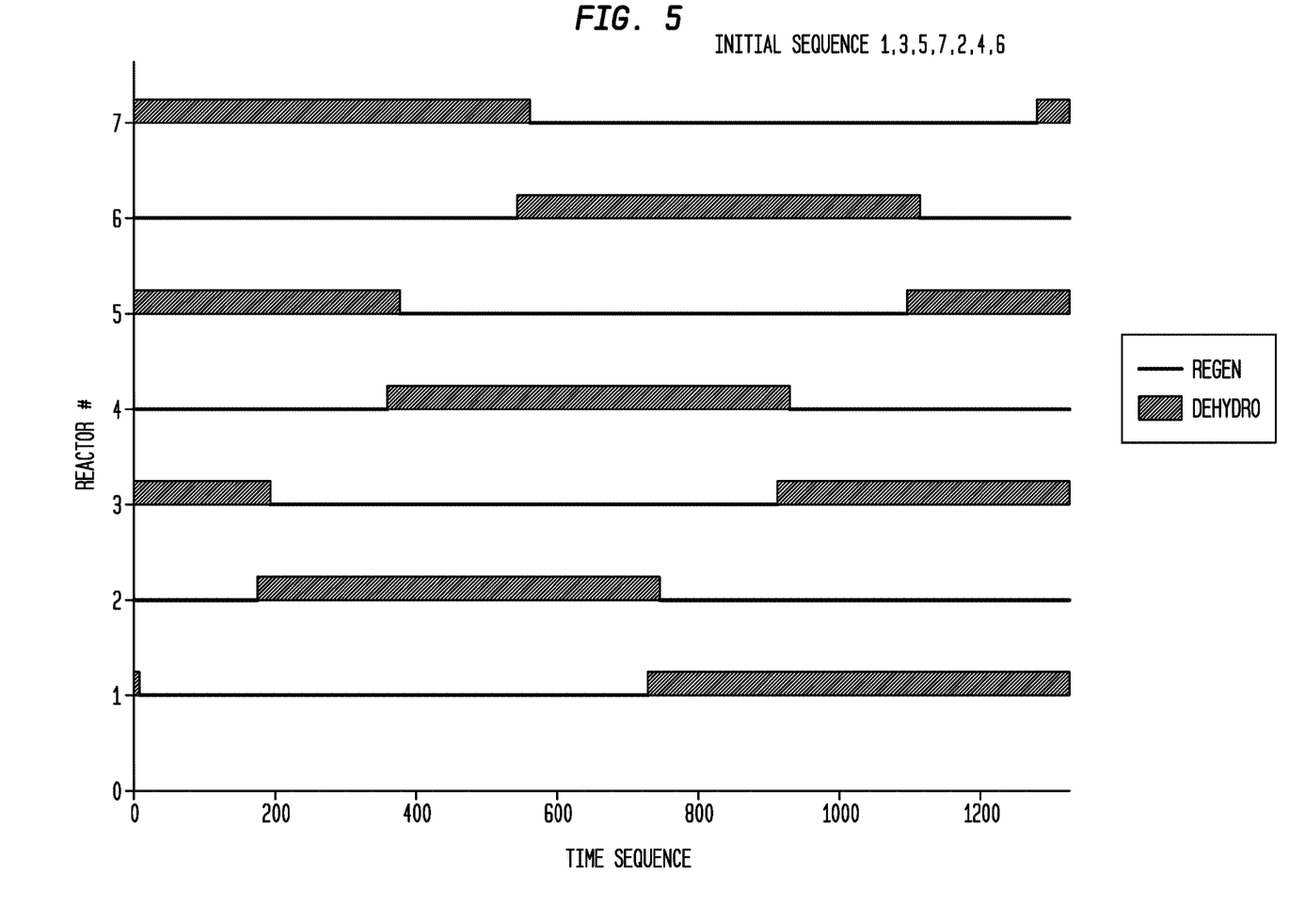
FIG. 5 is a diagram illustrating alternating production/regeneration times for seven reactors in a dehydrogenation system operating on a twenty-two (22) minute cycle in an initial sequence.
Figure 6:
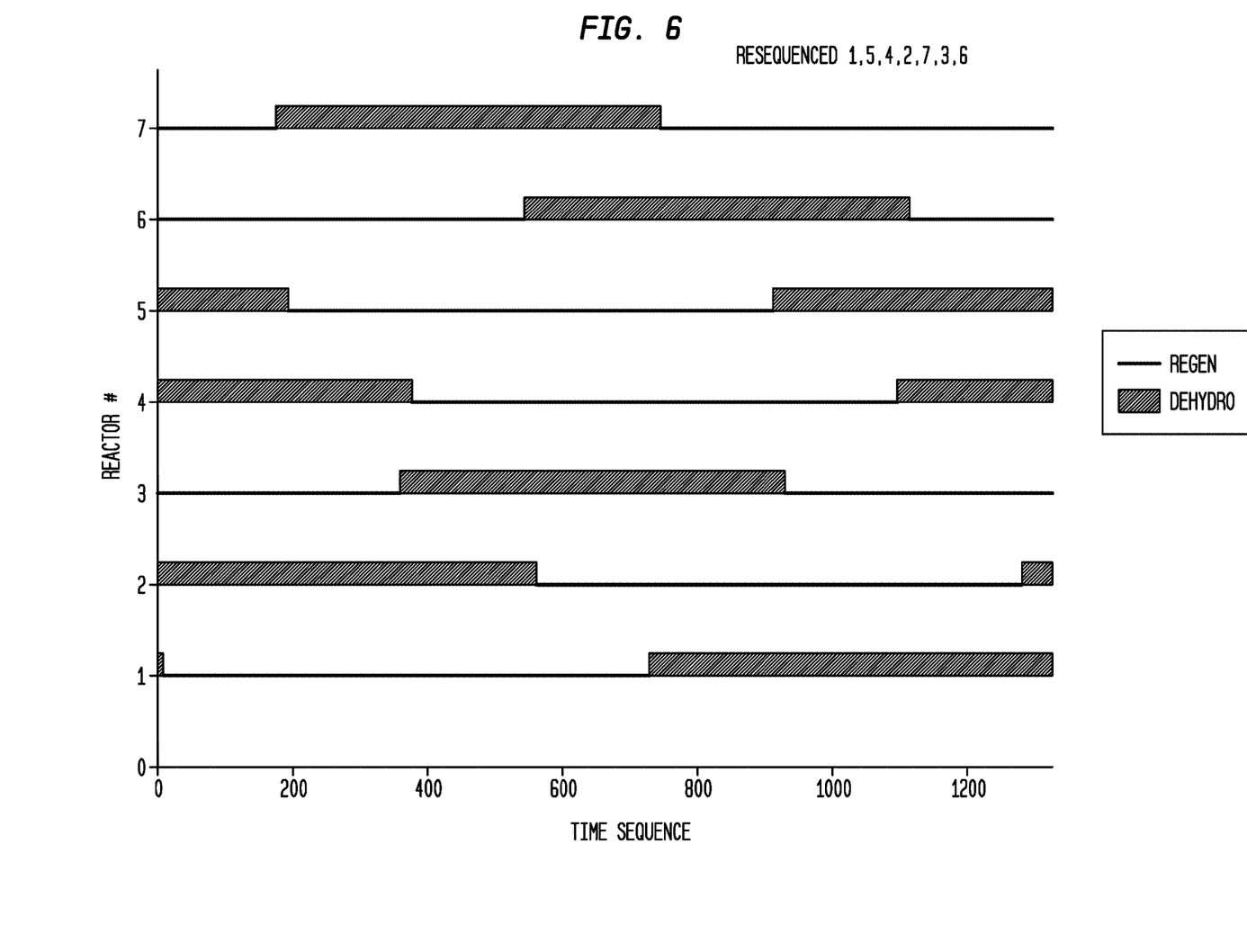
FIG. 6 is a diagram illustrating alternating production/regeneration times for seven reactors in a dehydrogenation system operating on a twenty-two (22) minute cycle after re-sequencing.

Complete repeating system cycles are shown in FIGS. 5 and 6. "Sequence", "re-sequence" and like terminology refers to the temporal order in which the various reactors are operated in a dehydrogenation mode before being switched to a regeneration mode of the reactor. Thus, FIG. 5 shows a reactor sequence for the system cycle of 7 reactors as 1, 3, 5, 7, 2, 4, 6, while FIG. 6 shows a reactor sequence of 1, 5, 4, 2, 7, 3, 6. When the timed sequence is completed, the system cycle is repeated.

The present invention may be applied to any suitable cyclical gas phase dehydrogenation process, for example, as described generally in U.S. Pat. No. 4,172,854 to Ellis et al. Dehydrogenation processes which may be re-sequenced in accordance with the invention thus include isobutane to isobutylene; butane to butenes and butadiene; propionitrile to acrylonitrile; propionaldehyde to acrolein; ethyl chloride to vinyl chloride; methyl isobutyrate to methyl methacylate; 2 or 3-chlorobutene-1 or 2,3-dichlorobutane to chloroprene; ethyl pyridine to vinyl pyridine; ethylbenzene to styrene; isopropylbenzene to α-methyl styrene; ethylchlorohexane to styrene; cyclohexane to benzene; ethane to ethylene to acetylene; propane to propylene or methyl acetylene or allene; isopentane to isoanylene and isoprene; n-butene to butadiene-1,3 and vinyl acetylene; methyl butene to isoprene; cyclopentane to cyclopentene and cyclopentadiene; n-octane to ethyl benzene and orthoxylene; monomethyl-heptanes to xylenes; ethyl acetate to vinyl acetate; 2,4,4-trimethylpentane to xylenes; and the like. The preferred compounds to be dehydrogenated are hydrocarbons with a particularly preferred class being acyclic non-quaternary hydrocarbons having 3 to 5 carbon atoms or ethyl benzene and the preferred products are isobutene, propene, n-butene-1 or 2, butadiene-1,3vinyl acetylene, 2-methyl-1-butene, 3-methyl-1-butene, 3-methyl-2-butene, isoprene, styrene or mixtures thereof. Especially preferred as feed are isobutane, n-butane, isopentane, ethyl benzene mixtures thereof such as hydrocarbon mixtures containing these compounds in at least 50 mol percent.

Suitable catalysts are described in Ullman's Encyclopedia of Industrial Chemistry, *Hydrogenation and Dehydrogenation*, Domenico Sanfilippo and Paul N. Rylander, Ed. Volume 18, PP. 451-471 Published Online: 15 Oct. 2009, DOI: 10.1002/14356007.a13_487.pub2, Copyright© 2002 by Wiley-VCH Verlag GmbH & Co. KgaA and the references cited therein.

Two large families of catalysts for the dehydrogenation of alkanes (based on Cr and Pt, respectively) do not differ substantially in terms of activity and selectivity but rather in the quality of some byproducts and in the treatment needed to complete the regeneration after the combustion of the coke. The maximum level of coke accumulation and consequently the time length needed for the reaction step before the regeneration depend on the nature of the particular catalyst used. In addition, the phenomena that lead to the irreversible deactivation (sintering, volatilization of the active components, and transformations of the morphology or the state of the support) are typically connected to the chemical types that characterize the various catalysts.

With respect to Chromium-Based Catalysts, two supports are most widely used, $ZrO_2$, which shows low acidity and high thermal stability, and transition aluminas (δ-θ), which are selected as actual supports for commercial catalysts. The catalyst formulation includes promotion with alkali metals, which is fundamental for increasing the chromium active sites and decreasing the surface acidity (of both chromium and aluminum oxides). Potassium has the best effect if provided in the right amount. Typically, a volcano-shape curve of activity and selectivity is obtained by increasing the potassium content. The nature of the active site is debated: $Cr^{3+}$, both $Cr^{3+}$ and $Cr^{2+}$, and coordinatively unsaturated $Cr^{2+}$ have been indicated as playing a role in the catalytic activity. For dehydrogenation of isobutane on $Cr_2O_3/Al_2O_3$, a Langmuir-Hinshelwood-type of kinetic equation is proposed, where it is assumed that the adsorption of isobutane represents the slow stage of the reaction and that no competition with adsorption of hydrogen exists.

With respect to Platinum-Tin-Based Catalysts, typically, Pt/Sn is supported either on alumina or on either $ZnAl_2O_4$ or $MgAl_2O_4$. The catalyst is promoted with alkali metals and further promoters. The role of Sn is to improve activity, selectivity, and stability because it neutralizes the acidity of supports, interacts electronically with Pt, and reduces the ensemble effect that favors coke formation. Increasing the loading of Pt+Sn, increasing the Sn/Pt ratio, or increasing the temperature of the reduction reaction causes the system to shift from separated phases towards the formation of Pt–Sn alloys. The catalyst preserves some bifunctional (acidic and noble-metal) activity, resulting in a moderate tendency to skeletal isomerization (e.g., isobutyl to n-butyl). Some characteristics of the catalysts have significant impact on the industrial implementation: The Pt/Sn catalysts undergo a double-mechanism ageing through coke fouling and sintering. The Pt/Sn catalysts can tolerate a coke build-up of several percentage points, preserving enough catalytic activity for allowing a period "on stream" of several hours/days before mandating a regeneration. The two promoted and optimized catalytic systems (Pt–Sn/$Al_2O_3$ and $Cr_2O_3$/$Al_2O_3$) show comparable performances in terms of selectivity to olefins. A periodical regeneration with air is mandatory for both catalysts to burn off the coke. The catalyst will therefore undergo a cycle during which it will be exposed to a hydrocarbon atmosphere, followed by a period in the presence of oxygen (and/or some steam). It must therefore keep its morphological, structural, and chemical stability under severe hydrothermal conditions. The length of the time on hydrocarbon stream is distinctive of the selected active phase: typical values are minutes/hours for Cr catalysts and hours/days for the Pt ones.

Likewise, gallium (Ga) catalysts may be employed, as is seen in United States Patent Application Publication No. 2019/0126242 of Xing et al. with or without additional catalyst metals present. See U.S. Pat. No. 5,219,816 to Zhou et al. which discloses Ga/Pt dehydrogenation catalysts.

The catalyst beds may be undiluted, i.e. consist entirely of the supported active catalyst, or diluted with inert material if so desired and/or include a heat-generating material as is disclosed in U.S. Pat. Nos. 7,622,623; 7,973,207; 8,188,328; and 9,725,380. The inert material may be, for example, a granular, alpha-alumina material of similar particle size to the supported catalyst. The heat generating material may include a metal selected from the group consisting of copper, chromium, molybdenum, vanadium, cerium, yttrium, scandium, tungsten, manganese, iron, cobalt, nickel, silver, bismuth and combinations thereof. Exemplary carriers for the heat-generating material include, but are not limited to, various aluminum oxides or hydroxides such as aluminum trihydroxide, boehmite, pseudo-boehmite, gibbsite, bayerite, transition aluminas or alpha-alumina, silica/alumina, silica, silicates, aluminates such as calcium aluminate or barium hexyluminate, calcined hydrotalcites, zeolites, zinc oxide, chromium oxides, magnesium oxides and combinations thereof. Optionally, the heat-generating material may further comprise a promoter, such as an alkali, an alkaline earth metal, lithium, sodium, potassium, rubidium, cesium, beryllium, magnesium, calcium, strontium, zirconium, barium and a combination thereof.

The dehydrogenation reaction may be carried out in a gas phase at atmospheric pressure, superatmospheric pressure or at sub-atmospheric pressure. The total pressure of the system will normally be about atmospheric pressure or sub-atmospheric pressure. Generally the total pressure will be between about 1 p.s.i.a. and about 75 p.s.i.a. Preferably, the total pressure will be less than about 50 p.s.i.a. The temperature of the dehydrogenation reaction will generally be in a range of about 350° C. to 700° C. with excellent results being obtained in the range of 400° C. to 650° C. The gaseous reactants can be conducted through the reaction chamber at a fairly wide range of flow rates. The optimum flow rates will be dependent upon such variables as the temperature of reaction, pressure, particle size of the catalyst, and so forth. Desirable flow rates may be established by one skilled in the art. Generally the flow rates will be within the range of about 0.10 to 10 liquid volumes of the organic compound to be dehydrogenated per volume of dehydrogenation zone containing catalyst per hour (referred to as LHSV). Usually the LHSV will be between 0.15 and about 5. For calculation, the volume of a fixed bed dehydrogenation zone containing the catalyst is that original void volume of reactor space containing catalyst. The dehydrogenation is carried out in a series of cycles which comprise dehydrogenation of a suitable feed over the catalysts of the invention under the conditions as defined for a period of time, usually about 6 to 12 minutes followed by a regeneration cycle during which the coke deposited from the dehydrogenation is burnt off. The regeneration can be longer or shorter than the dehydrogenation cycle as needed to remove the coke, usually about 6 to 12 minutes will be sufficient. The coke is removed by passing oxygen at a temperature of 550° C. to 650° C. over the catalyst. A convenient source of oxygen is air, however, pure oxygen or a mixture of oxygen with inert gases, such as nitrogen, either in the same or different proportions as air, can be used.

In a typical embodiment, at least two reactors are concurrently operated in a dehydrogenation production mode and at least two reactors are in various stages of regeneration. The overall repeating dehydrogenation/regeneration sequence for the system may be about 20-25 minutes for a chrome/alumina catalyzed fixed bed reactor. A typical cycle of each reactor includes operating the reactor in a dehydrogenation mode for about 10 minutes, followed by regeneration including sequentially a steam purge, regeneration with air and optionally fuel gas, evacuation, and catalyst reduction. Steam purging continues for about 1 minute, regeneration with air and optionally fuel gas is carried out for about 10 minutes, evacuation of the reactors is accomplished in about 30 seconds and the catalyst is reduced with hydrogen for about 1 minute. Suitable reaction systems which may be re-sequenced in accordance with the present invention include those seen in GB 794,089 and GB 823,626, as well as the reactor system shown schematically in FIGS. 2, 3 of the present application which is a chromia catalyzed gas phase dehydrogenation system for producing isobutylene from isobutane.

Figure 2:
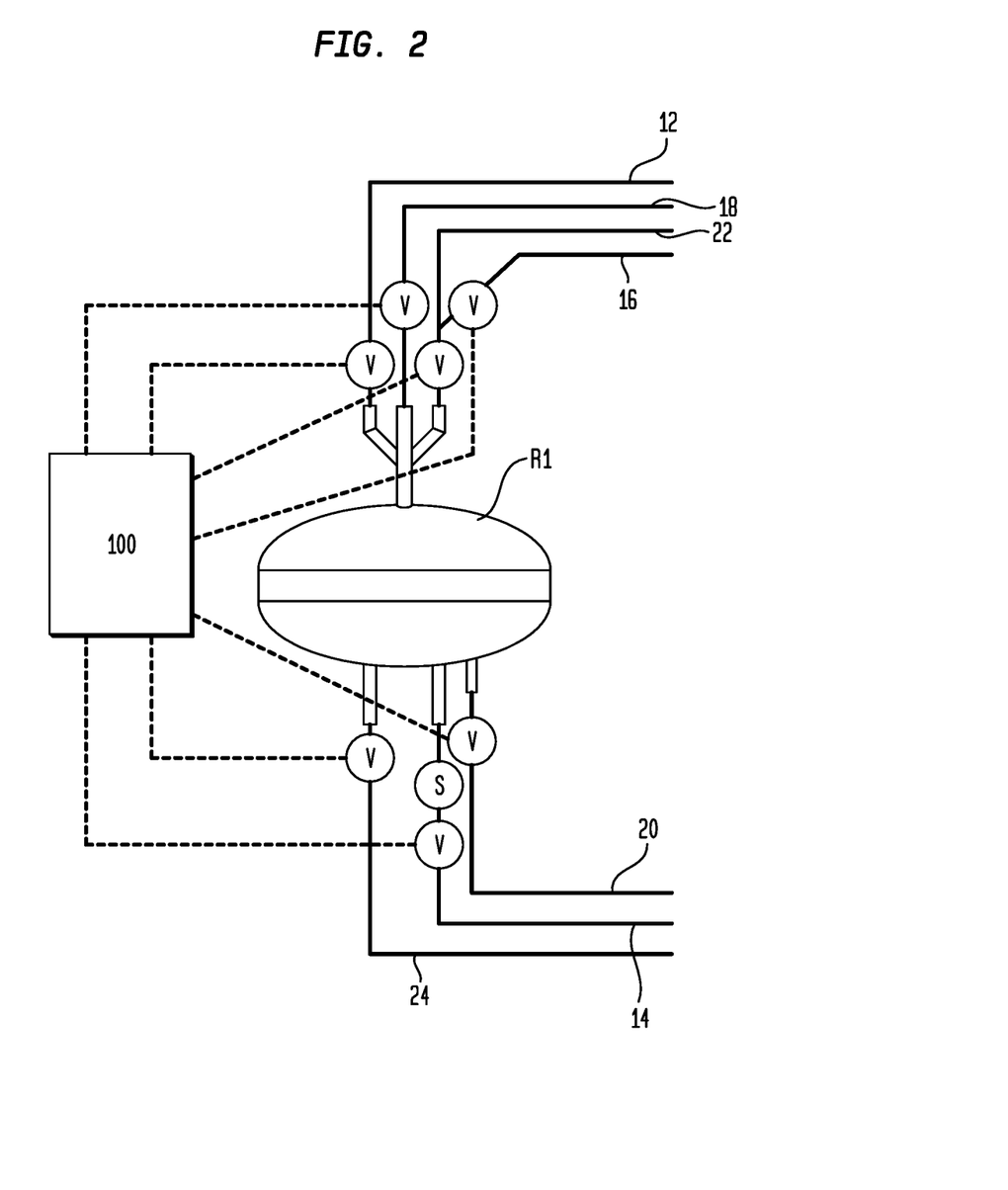
FIG. 2 is a schematic view of an individual dehydrogenation reactor connected to a digital controller as part of a battery of reactors in accordance with the present invention.
Figure 3:
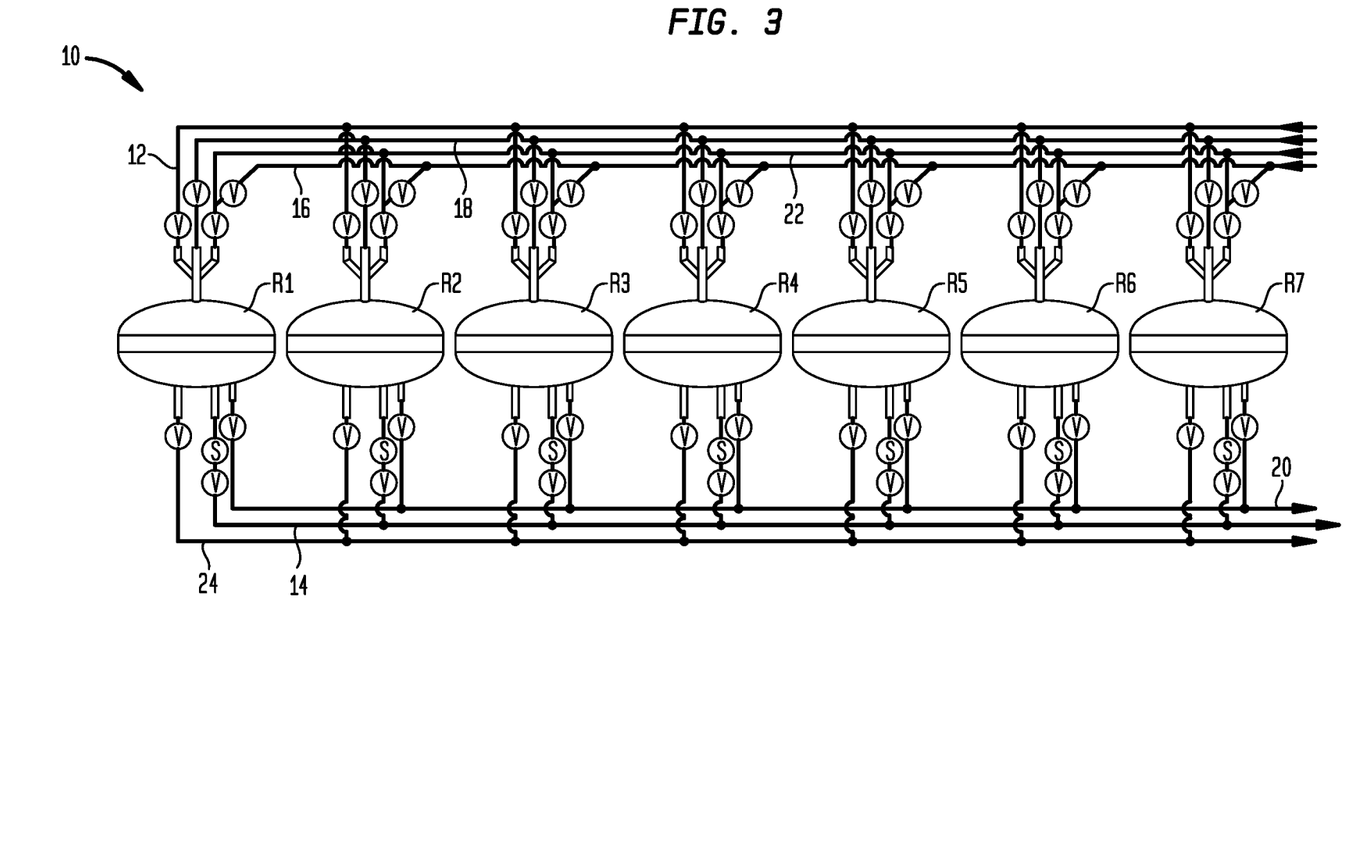
FIG. 3 is a partial schematic view showing a battery of reactors of the type shown in FIG. 2 (all of which are connected to the controller as in FIG. 2) which may be re-sequenced with the digital controller in accordance with the invention.

Referring to FIGS. 2, 3 there is shown in FIG. 2 a catalytic dehydrogenation reactor R1 connected in a battery of other reactors, R2 through R7, shown in FIG. 3. Reactor R1 is connected to a hydrocarbon charge feed line 12, a product discharge line 14, a steam line 16, an air regeneration line 18, a vacuum line 20, a reduction line 22, as well as a discharge line 24 for discharging of the gas from regeneration.

Operation of reactor R1 is controlled via a plurality of valves V and output from the reactor is sampled via a port S to determine productivity. The valves are connected to a digital controller 100 which sequences the various steps in each of the various reactors in the reaction system, as described below in connection with FIG. 3. Each of reactors R2 through R7 are likewise provided with valves V and a sampling port S and are connected to controller 100 in the same manner as R1 and operate the same way.

The system is conveniently controlled with a digital controller 100 connected to the valves, V, by way of dashed lines as indicated in the diagram. Connection to controller 100 are shown schematically only for the seven valves of reactor R1; it being appreciated that the valving on the other reactors is similarly connected and controlled by controller 100. Controller 100 is a DelataV DCS controller, model no. SD+ digital controller. If so desired, a second controller may be used to provide additional control integrity to critical features such as a Triconex controller, model 3008. Both can be utilized concurrently and are represented in the Figure collectively swimply as controller 100.

It is appreciated from the diagram, that resequencing is enabled by the digital controller, since 49 valves must be sequenced on the reactors alone in order to operate the system effectively.

As there is shown in FIG. 3, system 10 comprises seven reactors, R1 through R7, which are operated in a cycle such that three are simultaneously on stream for catalytic dehydrogenation, three are being subjected to regeneration of catalyst therein, and one is in a stage involving an operation such as evacuation, steam purge, hydrogen reduction or valve changes. The diagram in FIG. 5 shows how the reactors are operated on a twenty-two (22) minute (Appx.) cycle; it will be understood that the same operation can be carried out on a somewhat longer or a somewhat shorter cycle period. The diagrams and cycle times are shown in approximation, that is, cycle time for a single system cycle is conveniently represented in two modes, dehydrogenation extending to regeneration which, for purposes of FIGS. 5, 6, includes purging, air regeneration and reduction of the catalyst bed.

While it is seen in FIGS. 5, 6 that equal numbers of reactors are in dehydrogenation and regeneration modes at any given time in a cycle, the system may be sequenced such that more reactors are in dehydrogenation mode than regeneration mode at a given point in time in a cycle if so desired. That is FIGS. 5, 6 show roughly a 3-3-1 distribution between dehydrogenation and regeneration modes with one reactor in transition, however, the system could be sequenced in a 4-2-1 distribution between dehydrogenation and regeneration modes if that would provide better productivity balance in the system.

Referring again to FIGS. 2, 3, the hydrocarbon charge is fed to the battery of reactors by means of a line 12 connecting through suitable branch lines and valving arrangements to each of said reactors R1-R7 in the series; the motor operated valves therein being opened and closed at the appropriate time by the operation of a cycle controller 100. The hydrocarbon conversion products will be withdrawn from the system as by means of a line 14 also suitably connected with each of the reactors of the series by suitable branch lines and valving arrangement. The reactor effluent from line 14 is subjected to the series of steps for recovery of the desired products, including the use of a downstream product compressor and an absorber tower (not shown).

In order to purge the reactors and the catalyst herein at the end of the on-stream cycle, steam is admitted to the system as by means of a line 16 connected by suitable valved lines to each of the reactors R. Following the steam purge, a regenerating medium is introduced for removing contaminating deposit from the catalyst in the reactors, the medium being supplied to the appropriate reactor R1-R7 from a supply line 18 connected through suitable branch lines and valving arrangements for each of the reactors. Usually air or air diluted with flue gas is utilized as the regenerating medium, being raised to required temperature and pressure. While in some instances the reduction of the oxidized catalyst following regeneration can be effected by hydrocarbon charge, it is preferred in the operation of the present system to effect such reduction by means of hydrogen. Accordingly, following evacuation of the reactor subsequent to regeneration through line 20 and appropriate valve connections, hydrogen is admitted through line 22 and is appropriate connections. As shown, lines 16 and 22 connect with a single inlet to the reactor and appropriate valving provision is accordingly designed for the selective admission steam or hydrogen to that inlet.

The flue gas from regeneration is discharged through line 24 and its valved branch lines connecting to each of the reactors. Thus, as shown in FIGS. 5, 6, each reactor is on stream for dehydrogenation for 9-10 minutes and is on regeneration for 9-10 minutes or so including purging and valve changes. In other words, 40-50% of the total time of the cycle is devoted to actual on-stream production of desired hydrocarbon products while roughly equal time is used for regeneration, purging and valve operation. The system is conveniently controlled with a digital controller 100 connected to the valves, V, by way of dashed lines as indicated in the diagram. Connection to controller 100 are shown schematically only for the seven valves of reactor R1; it being appreciated that the valving on the other reactors is similarly connected and controlled by controller 100.

Figure 4:
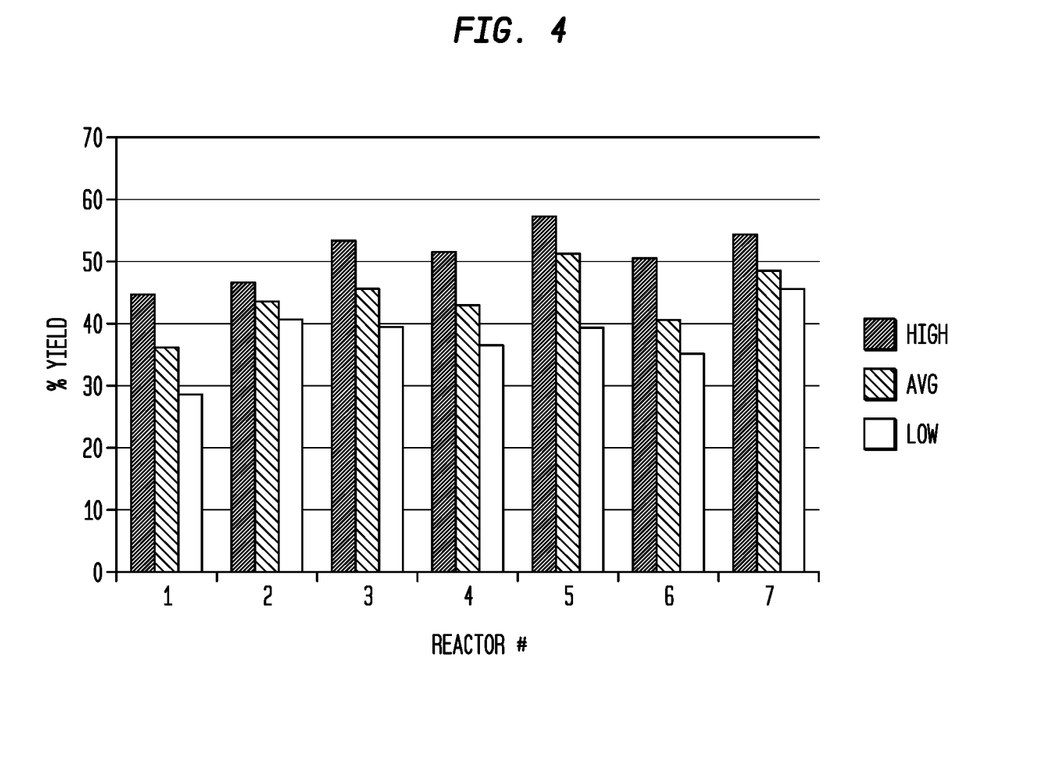
FIG. 4 is a histogram showing yield of each of the reactors of FIG. 3 during operation in a dehydrogenation mode.

Conventional operating systems for dehydrogenation systems with multiple synchronized reactors generally assume that the reactors, being more or less identical have more or less the same productivity, so that changing sequences is not necessary. The various reactors in the system have different productivities, even though they are of the same design. This is appreciated by reference to FIG. 4 which is a histogram of yields of reactors R1-R7 during operation in a roughly ten minute dehydrogenation mode during production. For purposes of determining production rates, average yields may be used. It is seen that yields may vary by ten percentage points or more.

The performance of each reactor in FIGS. 2, 3 is determined by sampling the branch lines from each reactor to output line 14 as indicated by the S designations and comparing with the hydrocarbon charge stream to the reactors. Means for determining reactor performance can be on-line or off line and include any suitable analytical technique such as chromatography, IR, or any suitable analytical technique. Sampling ports, S, may be used to obtain a sample for off-line or on-line analysis by chromatography, NMR, spectrometry and so forth, or may be used for determining productivity on-line by way of optical, infrared, or other spectral detectors, if so desired.

System 10 is operated such that the operating limit of the downstream product compressor (as well as the other components such as the regeneration air compressor) is capable of accommodating peak productivity during the 22 minute cycle. In an initial sequence shown in FIG. 1, peak production is seen at the beginning of a cycle and a yield delta of 8 or so is seen at mid-cycle. Once re-sequenced under the same operating conditions, one reduces the peak yield by around 2.5% corresponding to a productivity reduction of around 5% while lowering the yield delta as shown on FIG. 1. If productivity is increased by simply raising temperature, all other things being equal, productivity may be increased to the dashed line of FIG. 1 without exceeding the compressor limit. As shown on FIG. 1, peak yield is reduced 2.5%, so that productivity of the system can be increased 5.5%:

TABLE 1

| Re-Sequencing Productivity Increase | | |
| --- | --- | --- |
|  | Initial | Re-Sequenced |
| Average Yield (%) | 45.4 | 45.4 |
| Peak Yield (%) | 49.8 | 47.3 |
| Min Yield (%) | 42.0 | 43.7 |
| Yield delta (%) | 7.8 | 3.6 |
| Reduced Peak yield (%) |  | 2.5 |

While the initial and resequenced reactors have the same average yield, since the system can handle a peak yield value of approximately 50, productivity can be increased following resequencing by increasing feed rates of hydrocarbon, by raising temperature of the hydrocarbon charge, by raising the regeneration air temperature and so forth since the peak yield is reduced. The increased productivity thus realized=2.5/45.4 or 5.5%. An increase in productivity of 5.5% generates millions of dollars in additional revenue.

The reactor system of FIGS. 2, 3 was operated in a reactor cycle of approximately twenty-two (22) minutes in an initial reactor sequence wherein each reactor alternated between a dehydrogenation (production) mode and regeneration mode as indicated in Table 2 and FIG. 5. After determining the productivity of each reactor and system productivity when operating in the initial sequence, the system of FIG. 3 was re-sequenced to the sequence of Table 3 and FIG. 6. The re-sequencing and subsequent increase in productivity boosts output anywhere from about 2-10% and more using the same reactors, even though peak conversion is lower as noted above.

TABLE 2

Initial Reactor Sequence (1, 3, 5, 7, 2, 6)

| | Reactor # | | | | | | |
|---|---|---|---|---|---|---|---|
| | 1 | 2 | 3 | 4 | 5 | 6 | 7 |
| Dehydro Start (seconds) | 728 | 175 | 912 | 359 | 1096 | 543 | 1280 |
| Regen Start (seconds) | 8 | 745 | 193 | 930 | 377 | 1114 | 561 |

TABLE 3

Re-Sequenced System (1, 5, 4, 2, 7, 3, 6)

| | Reactor # | | | | | | |
|---|---|---|---|---|---|---|---|
| | 1 | 2 | 3 | 4 | 5 | 6 | 7 |
| Dehydro Start (seconds) | 728 | 1281 | 359 | 1096 | 912 | 543 | 175 |
| Regen Start (seconds) | 8 | 561 | 930 | 377 | 193 | 1114 | 745 |

Figure 7:
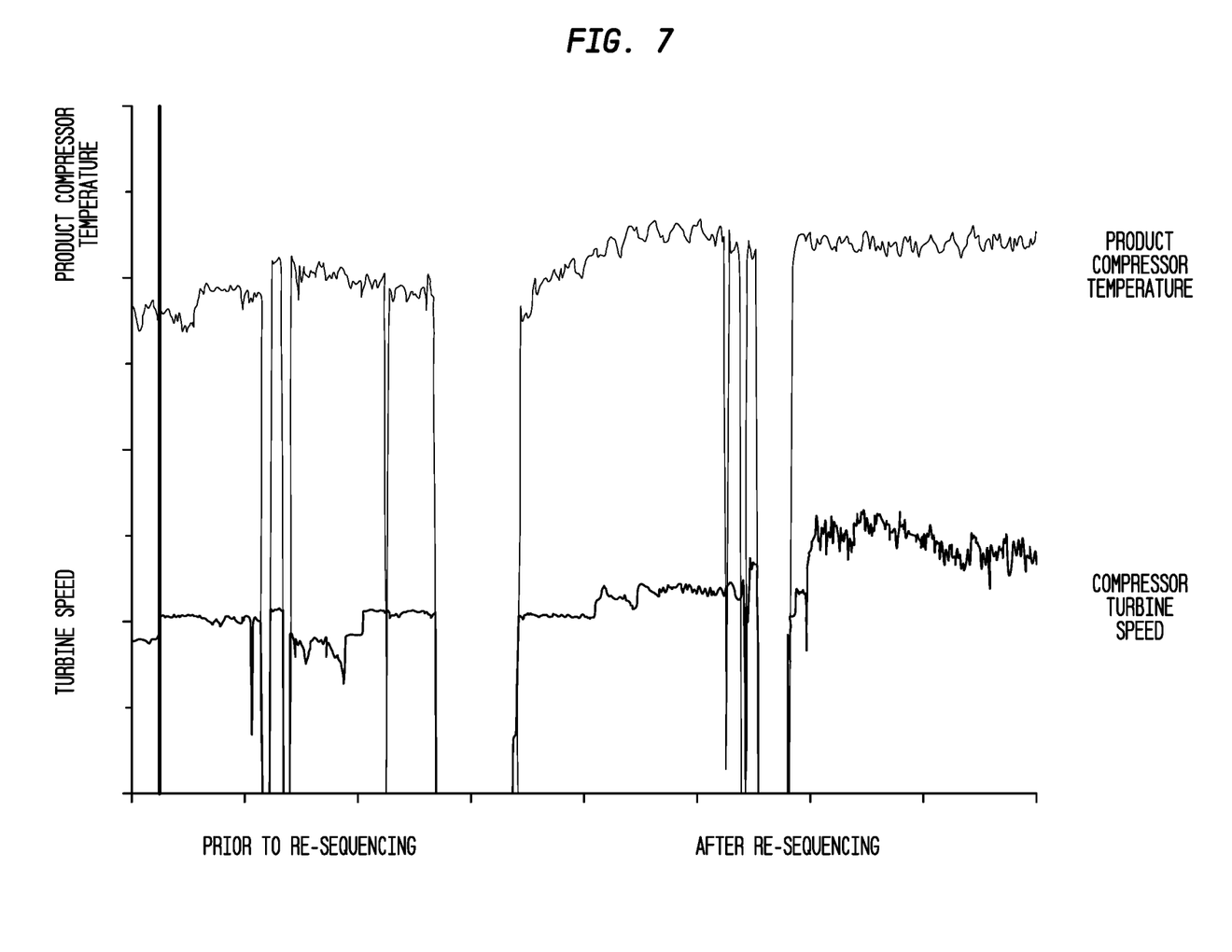
FIG. 7 is a diagram showing downstream product compressor temperature and turbine speed (first stage compressor) before and after re-sequencing.

By re-sequencing, it is possible to operate a downstream compressor at a higher rate and use higher regeneration air temperatures since it is not necessary to accommodate higher peak rates. This is shown in FIG. 7, which is a diagram showing downstream product compressor turbine speed and temperature before and after re-sequencing. The invention allows one to increase downstream turbine speed by 20% or more and raise temperatures by 10% or more without causing an upset in the system.

As is appreciated from the foregoing description and the appended drawings, the re-sequencing methodology is based on determining the productivity characteristics of each reactor and sequencing them so as to reduce system productivity deltas over the system cycle, including reducing peak rates. While any particular calculation method may be employed, it is particularly convenient to base re-sequencing calculations on yield data for all of the reactors for a given feed rate and set of operating conditions.

Generally speaking, the present invention is directed in a first aspect to a method of operating a dehydrogenation system with a plurality of dehydrogenation reactors alternating between dehydrogenation modes and regeneration modes in a timed sequence in a system cycle comprising: (a) operating the plurality of dehydrogenation reactors in an initial system sequence having an initial characteristic peak productivity over the course of a system cycle; (b) determining the productivity characteristics of each of the dehydrogenation reactors; (c) re-sequencing the reactors to operate in a second system sequence having a re-sequenced characteristic peak productivity lower than that of said initial characteristic peak productivity; and (d) increasing the re-sequenced characteristic peak productivity to a re-sequenced operating level to thereby increase system productivity over a system cycle as compared with operation in the initial system sequence.

The method of the first aspect of the invention may include one or more of the features listed in items 2 to 21 immediately below:

2. wherein the re-sequenced characteristic peak productivity is from 2% to 20% lower as compared to the initial characteristic peak productivity of the system.
3. wherein the re-sequenced characteristic peak productivity is from 3% to 6% lower as compared to the initial characteristic peak productivity of the system.
4. wherein peak productivities are determined from yield of dehydrogenation product.
5. wherein the re-sequenced reactors have a characteristic productivity delta lower than a characteristic productivity delta of the initial system sequence.
6. wherein the characteristic productivity delta of the re-sequenced system is at least 25% lower as compared to the characteristic productivity delta of the initial system sequence.
7. wherein the characteristic productivity delta of the re-sequenced system is at least 40% lower as compared to the characteristic productivity delta of the initial system sequence.
8. wherein the characteristic productivity deltas are determined from differences in yield of product.
9. wherein the step of increasing the re-sequenced characteristic peak productivity to the re-sequenced operating level includes: (i) raising a temperature of regeneration air or (ii) raising a temperature of a hydrocarbon feed or (iii) increasing a feed rate of hydrocarbon charge to the dehydrogenation system or (iv) decreasing an inlet pressure to the dehydrogenation system or (v) combinations of two or more of items (i) to (iv).
10. wherein the dehydrogenation system has from 3 to 12 reactors.
11. wherein the dehydrogenation system has from 5 to 10 reactors.
12. wherein a hydrocarbon charge to the reactor comprises an alkane.
13. wherein a hydrocarbon charge to the reactor comprises a butane.
14. wherein a hydrocarbon charge to the reactor comprises isobutane.
15. wherein the reactors contain fixed beds of catalyst selected from supported chromium catalysts, supported platinum-tin catalysts and supported gallium metal containing catalysts.
16. wherein a catalyst support is selected from alumina, $ZrO_2$, $ZnAl_2O_4$ and $MgAl_2O_4$.
17. wherein a hydrocarbon charge is provided to each reactor at a liquid hourly space velocity of from 0.15 to 5.
18. wherein the reactors are operated in a dehydrogenation mode at a reactor temperature of from 350° C. to 700° C.
19. wherein the reactors are regenerated with air at a temperature of from about 550° C. to about 700° C.
20. wherein each reactor is operated in a dehydrogenation mode within a system cycle for a duration of from 5 minutes to about 15 minutes.
21. wherein more reactors are operated in a dehydrogenation mode than in a regeneration mode at the same time within the system cycle.

A second aspect of the invention is directed to a method of operating a dehydrogenation system with a plurality of dehydrogenation reactors alternating between dehydrogenation modes and regeneration modes in a timed sequence in a system cycle comprising: (a) determining the productivity characteristics of each of said plurality of reactors; and (b) sequencing the reactors in the system cycle to achieve a productivity delta over the system cycle which is below a predetermined value.

The method of the second aspect of the invention may include one or more of the features listed in items 23 to 37 immediately below:

23. wherein the characteristic productivity delta of the re-sequenced system is less than 25% of a characteristic peak productivity of the system cycle.
24. wherein the characteristic productivity delta of the re-sequenced system less than 12.5% of a characteristic peak productivity of the system cycle.
25. wherein the characteristic productivity deltas are determined from differences in yield of product.
26. wherein the dehydrogenation system has from 3 to 12 reactors.
27. wherein the dehydrogenation system has from 5 to 10 reactors.
28. wherein a hydrocarbon charge to the reactor comprises an alkane.
29. wherein a hydrocarbon charge to the reactor comprises a butane.
30. wherein a hydrocarbon charge to the reactor comprises isobutane.
31. wherein the reactors contain fixed beds of catalyst selected from supported chromium catalysts, supported platinum-tin catalysts and supported gallium metal containing catalysts.
32. wherein the catalyst support is selected from alumina, $ZrO_2$, $ZnAl_2O_4$ and $MgAl_2O_4$.
33. wherein a hydrocarbon charge is provided to each reactor at a liquid hourly space velocity of from 0.15 to 5.
34. wherein the reactors are operated in a dehydrogenation mode at a reactor temperature of from 350° C. to 700° C.
35. wherein the reactors are regenerated with air at a temperature of from about 550° C. to about 700° C.
36. wherein each reactor is operated in a dehydrogenation mode within a system cycle for a duration of from 5 minutes to about 15 minutes.
37. wherein more reactors are operated in a dehydrogenation mode than in a regeneration mode at the same time within the system cycle.

A third aspect of the invention includes a dehydrogenation system comprising: (a) a plurality of dehydrogenation reactors valved to operate in alternating dehydrogenation modes and regeneration modes in a timed sequence in a system cycle by way of the plurality of valves; (b) a digital controller connected to the plurality of valves for sequencing the reactors; and (c) means for determining the productivity characteristics of each reactor over a system cycle. The digital controller is operable to re-sequence the reactors to reduce either peak productivity or productivity deltas over a system cycle.

The system of the third aspect of the invention may include one or more of the features listed in items 39 to 46 immediately below:

39. wherein the dehydrogenation system has from 3 to 12 reactors.
40. wherein the dehydrogenation system has from 5 to 10 reactors.
41. wherein the dehydrogenation system includes a hydrocarbon charge to the reactor comprising an alkane.
42. wherein the dehydrogenation system includes a hydrocarbon charge to the reactor comprising a butane.
43. wherein the dehydrogenation system includes a hydrocarbon charge to the reactor comprising isobutane.
44. wherein the reactors contain fixed beds of catalyst selected from supported chromium catalysts, supported platinum-tin catalysts and supported gallium metal containing catalysts.
45. wherein the catalyst support is selected from alumina, $ZrO_2$, $ZnAl_2O_4$ and $MgAl_2O_4$.
46. wherein more reactors are operated in a dehydrogenation mode than in a regeneration mode at the same time within the system cycle.

In a fourth aspect of the invention there is provided in a dehydrogenation system with a plurality of dehydrogenation reactors alternating between dehydrogenation modes and regeneration modes in a timed sequence in a repeating system cycle, the improvement comprising (a) determining the productivity characteristics of each of the dehydrogenation reactors and (b) re-sequencing the reactors such that a characteristic productivity delta over the repeating re-sequenced system cycle is below a predetermined value, wherein at least two reactors are operating in dehydrogenation modes at all times in the re-sequenced cycle.

The improvement of the fourth aspect of the invention may include one or more of the features listed in items 48 to 50 immediately below:

48. wherein re-sequencing the reactors comprises reducing the number of reactors operating in the system.
49. further comprising increasing the productivity of the re-sequenced system by (i) raising a temperature of regeneration air or (ii) raising a temperature of a hydrocarbon feed or (iii) increasing a feed rate of hydrocarbon charge to the dehydrogenation system or (iv) decreasing an inlet pressure to the dehydrogenation system or (v) combinations of two or more of items (i) to (iv).
50. wherein the characteristic productivity delta of the re-sequenced system is less than 12.5% of the characteristic peak productivity of the re-sequenced system repeating cycle.

While the invention has been described in detail, modifications within the spirit and scope of the invention will be readily apparent to those of skill in the art. Such modifications are also to be considered as part of the present invention. In view of the foregoing discussion, relevant knowledge in the art and references discussed above in connection with the Background of the Invention and Detailed Description, the disclosures of which are all incorporated herein by reference, further description is deemed unnecessary. In addition, it should be understood from the foregoing discussion that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A method of operating a dehydrogenation system with a plurality of dehydrogenation reactors alternating between dehydrogenation modes and regeneration modes in a timed sequence in a repeating system cycle comprising:
    (a) operating the plurality of dehydrogenation reactors in an initial system sequence having an initial characteristic peak productivity over the course of a system cycle;
    (b) determining the productivity characteristics of each of the dehydrogenation reactors;
    (c) re-sequencing the reactors to operate in a second system sequence having a re-sequenced characteristic peak productivity lower than that of said initial characteristic peak productivity, wherein the second system sequence has a different temporal order in which the reactors are operated in said dehydrogenation mode before being switched to said regeneration mode than the initial system sequence; and (d) increasing the re-sequenced characteristic peak productivity to a re-sequenced operating level to thereby increase system productivity over a system cycle as compared with operation in the initial system sequence.

2. The method of operating a dehydrogenation system with a plurality of dehydrogenation reactors alternating between dehydrogenation modes and regeneration modes in a timed sequence in a repeating system cycle according to claim 1, wherein peak productivities are determined from yield of dehydrogenation product.

3. The method of operating a dehydrogenation system with a plurality of dehydrogenation reactors alternating between dehydrogenation modes and regeneration modes in a timed sequence in a repeating system cycle according to claim 1, wherein the re-sequenced reactors have a characteristic productivity delta lower than a characteristic productivity delta of the initial system sequence.

4. The method of operating a dehydrogenation system with a plurality of dehydrogenation reactors alternating between dehydrogenation modes and regeneration modes in a timed sequence in a repeating system cycle according to claim 3, wherein the characteristic productivity deltas are determined from differences in yield of product.

5. The method of operating a dehydrogenation system with a plurality of dehydrogenation reactors alternating between dehydrogenation modes and regeneration modes in a timed sequence in a repeating system cycle according to claim 1, wherein the step of increasing the re-sequenced characteristic peak productivity to the re-sequenced operating level includes: (i) raising a temperature of regeneration air or (ii) raising a temperature of a hydrocarbon feed or (iii) increasing a feed rate of hydrocarbon charge to the dehydrogenation system or (iv) decreasing an inlet pressure to the dehydrogenation system or (v) combinations of two or more of items (i) to (iv).

6. The method of operating a dehydrogenation system with a plurality of dehydrogenation reactors alternating between dehydrogenation modes and regeneration modes in a timed sequence in a repeating system cycle according to claim 1, wherein the dehydrogenation system has from 5 to 10 reactors.

7. The method of operating a dehydrogenation system with a plurality of dehydrogenation reactors alternating between dehydrogenation modes and regeneration modes in a timed sequence in a repeating system cycle according to claim 1, wherein a hydrocarbon charge to the reactors comprises isobutane.

8. The method of operating a dehydrogenation system with a plurality of dehydrogenation reactors alternating between dehydrogenation modes and regeneration modes in a timed sequence in a repeating system cycle according to claim 1, wherein the reactors contain fixed beds of catalyst selected from supported chromium catalysts, supported platinum-tin catalysts and supported gallium metal containing catalysts.

9. The method of operating a dehydrogenation system with a plurality of dehydrogenation reactors alternating between dehydrogenation modes and regeneration modes in a timed sequence in a repeating system cycle according to claim 8, wherein the catalyst support is selected from alumina, $ZrO_2$, $ZnAl_2O_4$ and $MgAl_2O_4$.

10. A method of operating a dehydrogenation system with a plurality of dehydrogenation reactors alternating between dehydrogenation modes and regeneration modes in a timed sequence in a repeating system cycle comprising:

(a) operating the plurality of dehydrogenation reactors in an initial system sequence having an initial characteristic peak productivity over the course of a system cycle;

(b) determining the productivity characteristics of each of the dehydrogenation reactors;

(c) re-sequencing the reactors to operate in a second system sequence having a re-sequenced characteristic peak productivity lower than that of said initial characteristic peak productivity; and (d) increasing the re-sequenced characteristic peak productivity to a re-sequenced operating level to thereby increase system productivity over a system cycle as compared with operation in the initial system sequence, wherein the re-sequenced characteristic peak productivity is from 2% to 20% lower as compared to the initial characteristic peak productivity of the system.

11. The method of operating a dehydrogenation system with a plurality of dehydrogenation reactors alternating between dehydrogenation modes and regeneration modes in a timed sequence in a repeating system cycle according to claim 10, wherein the re-sequenced characteristic peak productivity is from 3% to 6% lower as compared to the initial characteristic peak productivity of the system.

12. A method of operating a dehydrogenation system with a plurality of dehydrogenation reactors alternating between dehydrogenation modes and regeneration modes in a timed sequence in a repeating system cycle comprising:

(a) operating the plurality of dehydrogenation reactors in an initial system sequence having an initial characteristic peak productivity over the course of a system cycle;

(b) determining the productivity characteristics of each of the dehydrogenation reactors;

(c) re-sequencing the reactors to operate in a second system sequence having a re-sequenced characteristic peak productivity lower than that of said initial characteristic peak productivity; and (d) increasing the re-sequenced characteristic peak productivity to a re-sequenced operating level to thereby increase system productivity over a system cycle as compared with operation in the initial system sequence, wherein the characteristic productivity delta of the re-sequenced system is at least 25% lower as compared to the characteristic productivity delta of the initial system sequence.

13. The method of operating a dehydrogenation system with a plurality of dehydrogenation reactors alternating between dehydrogenation modes and regeneration modes in a timed sequence in a repeating system cycle according to claim 12, wherein the characteristic productivity delta of the re-sequenced system is at least 40% lower as compared to the characteristic productivity delta of the initial system sequence.

14. A method of operating a dehydrogenation system with a plurality of dehydrogenation reactors alternating between dehydrogenation modes and regeneration modes in a timed sequence in a repeating system cycle comprising:

(a) determining the productivity characteristics of each of said plurality of reactors; and (b) re-sequencing the reactors in the system cycle to achieve a characteristic productivity delta over the system cycle which is below a predetermined value, and wherein the characteristic productivity delta of the re-sequenced system is less than 25% of a characteristic peak productivity of the system cycle.

15. The method of operating a dehydrogenation system with a plurality of dehydrogenation reactors alternating between dehydrogenation modes and regeneration modes in a timed sequence in a repeating system cycle according to claim 14, wherein the characteristic productivity delta of the re-sequenced system less than 12.5% of a characteristic peak productivity of the system cycle.

16. A dehydrogenation system comprising:
   (a) a plurality of dehydrogenation reactors valved to operate in alternating dehydrogenation modes and regeneration modes in a timed initial sequence in a system cycle by way of the plurality of valves;
   (b) a programmable digital controller connected to the plurality of valves for sequencing the reactors; and
   (c) means for determining the productivity characteristics of each reactor over a system cycle, wherein the programmable digital controller is operable to re-sequence the reactors to a second system sequence to reduce either characteristic peak productivity or characteristic productivity deltas over a system cycle and wherein the second system sequence has a different temporal order in which the reactors are operated in said dehydrogenation mode before being switched to said regeneration mode than the initial system sequence.

17. The dehydrogenation system according to claim 16, wherein the dehydrogenation system has from 3 to 12 reactors.

18. The dehydrogenation system according to claim 17, wherein the dehydrogenation system has from 5 to 10 reactors.

19. The dehydrogenation system comprising according to claim 16, wherein the reactors contain fixed beds of catalyst selected from supported chromium catalysts, supported platinum-tin catalysts and supported gallium metal containing catalysts.

* * * * *